United States Patent
Bosselaar et al.

(10) Patent No.: US 6,773,421 B2
(45) Date of Patent: Aug. 10, 2004

(54) COMBINATION FOR MANAGING THE INVOLUNTARY LOSS OF BLADDER CONTROL

(75) Inventors: Cornelis Jacobus Bosselaar, Appleton, WI (US); John Anthony Rooyakkers, Little Chute, WI (US); Jeremy Thaddeus Gauger, Appleton, WI (US)

(73) Assignee: Kimberly-Clark Worlwide, Inc., Neenah, WI (US)

( * ) Notice: Subject to any disclaimer, the term of this patent is extended or adjusted under 35 U.S.C. 154(b) by 215 days.

(21) Appl. No.: 10/020,455

(22) Filed: Dec. 14, 2001

(65) Prior Publication Data

US 2003/0114823 A1 Jun. 19, 2003

(51) Int. Cl.⁷ .......................... A61F 13/15; A61L 15/00
(52) U.S. Cl. .......................... 604/385.02; 604/385.06; 206/348
(58) Field of Search .......................... 604/360, 385.01, 604/385.02, 385.06, 385.17, 904; 206/438

(56) References Cited

U.S. PATENT DOCUMENTS

| | | | |
|---|---|---|---|
| 5,569,230 A | * 10/1996 | Fisher et al. | 604/385.06 |
| 5,827,251 A | 10/1998 | Moder et al. | |
| 5,839,585 A | 11/1998 | Miller | |
| 5,865,322 A | 2/1999 | Miller | |
| 5,939,426 A | * 8/1999 | McCullough | 514/290 |
| 5,947,302 A | 9/1999 | Miller | |
| 5,964,741 A | 10/1999 | Moder et al. | |
| 5,986,165 A | * 11/1999 | Moder et al. | 604/358 |
| 6,004,307 A | * 12/1999 | Colon et al. | 604/358.06 |
| 6,090,038 A | 7/2000 | Zunker et al. | |
| 6,090,098 A | 7/2000 | Zunker et al. | |
| 6,142,928 A | 11/2000 | Zunker et al. | |
| 6,183,456 B1 | 2/2001 | Brown et al. | |
| 6,229,061 B1 | 5/2001 | Dragoo et al. | |
| 6,248,359 B1 | 6/2001 | Faour | |
| 6,262,115 B1 | 7/2001 | Guittard et al. | |
| 6,350,931 B1 | * 2/2002 | Martin | 604/358 |
| 6,352,528 B1 | * 3/2002 | Weber et al. | 604/385.03 |
| 6,500,160 B2 | * 12/2002 | Mizutani et al. | 604/385.02 |
| 6,616,643 B1 | * 9/2003 | Costa | 604/385.02 |
| 2001/0003152 A1 | * 6/2001 | Lee | 604/385.02 |
| 2001/0056270 A1 | * 12/2001 | Mizutani et al. | 604/385.02 |
| 2002/0121292 A1 | 9/2002 | Betrabet et al. | |
| 2002/0156448 A1 | * 10/2002 | Steger et al. | 604/385.06 |
| 2003/0023217 A1 | * 1/2003 | McManus et al. | 604/385.01 |
| 2003/0065301 A1 | * 4/2003 | Elliott et al. | 604/385.06 |
| 2003/0088224 A1 | * 5/2003 | Cerman et al. | 604/385.01 |
| 2003/0097108 A1 | * 5/2003 | Hasse et al. | 604/379 |
| 2003/0102238 A1 | * 6/2003 | White et al. | 206/438 |

FOREIGN PATENT DOCUMENTS

| | | |
|---|---|---|
| EP | 0767659 B1 | 10/1999 |
| EP | 1 013 249 A1 | 6/2000 |
| GB | 2 238 286 A | 5/1991 |
| WO | WO 97/45089 | 12/1997 |
| WO | WO 98/11888 | 3/1998 |
| WO | WO 00/12069 | 3/2000 |

* cited by examiner

Primary Examiner—John J. Calvert
Assistant Examiner—Michael G. Bogart
(74) Attorney, Agent, or Firm—Thomas J. Connelly

(57) ABSTRACT

A combination for managing the involuntary loss of bladder control is disclosed along with a method of using and manufacturing the combination. The combination includes an anti-incontinent agent capable of reducing urinary loss and an absorbent article capable of absorbing urine that is lost from the body. The anti-incontinent agent is enclosed in a first wrapper and the absorbent article is positioned adjacent to the wrapped anti-incontinent agent. A pouch encloses the wrapped anti-incontinent agent and the absorbent article to keep both items sanitary. A combination of a disposable absorbent article and information related to an anti-incontinent agent is also disclosed.

21 Claims, 6 Drawing Sheets

COMBINATION FOR MANAGING THE INVOLUNTARY LOSS OF BLADDER CONTROL

BACKGROUND OF THE INVENTION

Urinary incontinence is an involuntary leaking of urine, which can occur when any of the normal functions of the bladder are disrupted. There are three major categories of urinary incontinence, which are classified according to etiology: stress incontinence (SI), also referred to as genuine stress incontinence; detrusor instability (DI), also referred to as urge incontinence (UI); and overflow incontinence. In addition, many patients, especially women who have given birth to one or more children, and older women are diagnosed with mixed incontinence, such as a combination of stress incontinence and urge incontinence.

The primary etiological factor producing SI is the incomplete transmission of abdominal pressure to the proximal urethra due to displacement from its intra-abdominal position. SI is classified as a failure to store urine. In this type of urinary dysfunction, leakage occurs during times of abdominal pressure or "stress" such as coughing, sneezing, laughing, bending or lifting heavy objects. The frequency and severity of such urine loss can increase as the muscles and tissues, particularly those near the urethro-vaginal myofascial area, grow weaker. It has also been recognized that the urinary sphincter muscle, which is located at the upper end of the urethra, adjacent to the bladder, works well at sealing off the passing of urine from the bladder to the urethra when it has a generally round or circular cross-sectional configuration. Support of the proximal urethra elevates it above the pelvic floor and subjects it to increases in intra-abdominal pressure, thus allowing compression and maintenance of continence. However, when this passageway becomes distorted into an elliptical or oval cross-sectional configuration, the sphincter muscle can not close properly, therefore, the tendency for involuntary urine loss increases. SI can be caused by damage to the proximal urethra through trauma, radiation, sacral spinal cord lesions, prior surgeries, estrogen deficiency, or a congenital weakness. Neuromuscular damage from pregnancy, childbirth, and pelvic surgery is a common cause of SI. SI may also occur in men who have undergone prostatectomy, since the procedure may damage the proximal urethra.

The most common type of urge incontinence (UI) in elderly individuals is detrusor instability (DI) or "urge" incontinence. DI is urinary leakage due to spontaneous and uninhibited detrusor contractions occurring before the bladder is completely full. Accompanying these contractions is an extremely strong need to urinate (urgency) and in some case complaints of frequency or nocturia. Another term often used is overactive bladder, which includes a cluster of symptoms; urgency, frequency, nocturia and in some cases DI. Most of the time the cause of DI is idiopathic, unless there is a presence of neurological dysfunction such as associated with stroke, cerebral tumors, Parkinson's diseases, multiple sclerosis, or Alzheimer's disease. However, a tumor, stone, foreign body, urinary tract infection or even prior surgical procedures to reduce incontinence can also cause this condition.

Overflow incontinence is the involuntary loss of urine associated with an over-distended bladder. This condition results in frequent to constant dribbling of urine in the absence of detrusor contractions. Symptoms may resemble those seen in SI or DI. In men, overflow incontinence may be due to an outlet obstruction, hypocontracted detrusor muscle, or a neurological disorder such as a spinal cord injury or multiple sclerosis. Although rarely seen in women, overflow incontinence is most commonly due to prior genitourinary surgery or pelvic organ prolapse. Individuals with overflow incontinence will typically retain large amounts of urine within the bladder after voiding. In this case, the ability to store urine is intact but bladder emptying is impaired.

Although urinary incontinence affects individuals of all ages, the majority of people are elderly and women. Among non-institutionalized people over 60 years of aged, the prevalence of UI ranges from 15 to 35 percent with women having twice the prevalence of men. Among institutionalized people, this number jumps significantly, as it is often the primary reason why individuals move to institutions. Urinary incontinence is also prevalent in the younger population affecting 10 to 30 percent of women and 1.5 to 5 percent of men.

Unfortunately, the social stigma and embarrassment associated with urinary incontinence contribute greatly to the distress, depression, isolation, and social withdrawal experienced by some affected individuals. Local complications such as skin breakdown, leading to bedsores and infection can also occur. In addition to the social and physical complications, the financial costs are enormous. UI is the second-leading cause of nursing home admissions and accounts for a large percentage of these health care costs. The annual costs of caring for both ambulatory and institutionalized persons with incontinence, including indirect costs (e.g. the treatment of injuries resulting from falls and complications such as skin breakdown), is estimated at several billion dollars.

Accordingly, there is a need for improved ways for individuals to manage their incontinence without embarrassment and with dignity and discreteness so that they may continue to lead active lives and enjoy a high quality of life. Specifically, because there are many mechanisms to maintain continence, involving the bladder, urethra, spinal cord and brain, it follows that a single tactic is often not enough to eliminate the possibility of involuntarily urine loss and soiling of one's clothing. Since no one single drug, device, or absorbent article can completely assure an individual of the impossibility of the embarrassment of an incontinent episode, a need exists to use anti-incontinence agents and absorbent articles in combination. A further need exists to provide the convenience of an incontinence prevention system to reduce the frequency of incontinent episodes and to protect a users' clothing from urine that is lost in one package. A combination of an anti-incontinence agent and an absorbent article provides individuals with a discreet, convenient and sanitary approach to manage their incontinence without the need for institutionalization or undue involvement by a medical professional.

SUMMARY OF THE INVENTION

Briefly, this invention relates to a combination for managing the involuntary loss of bladder control along with a method of using and manufacturing the combination. The combination includes an anti-incontinent agent capable of reducing urinary loss and an absorbent article capable of absorbing urine that is lost from the body. The anti-incontinent agent is enclosed in a first wrapper and the absorbent article is positioned adjacent to the wrapped anti-incontinent agent. A pouch encloses the wrapped anti-incontinent agent and the absorbent article to keep both items sanitary. A combination of a disposable absorbent article and information related to an anti-incontinent agent is also disclosed.

DETAILED DESCRIPTION OF THE PREFERRED EMBODIMENTS

Figure 1:
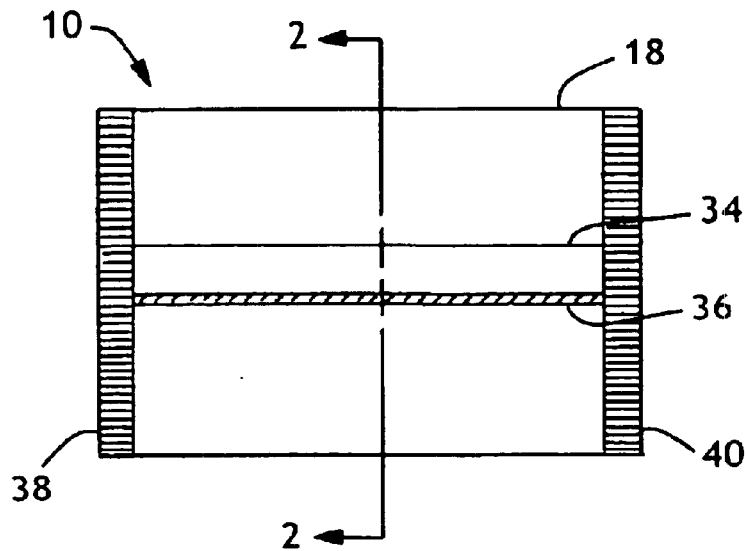
FIG. 1 is a front view of a pouch containing the combination.

Referring now to FIGS. 1–3, and 5, a combination 10 is depicted which includes an anti-incontinence agent 12 which is enclosed in a first wrapper 14 and an absorbent article 16. The absorbent article 16 is located adjacent to the wrapped anti-incontinence agent 12 and may be enclosed in a second wrapper 42, as specifically shown in FIG. 3. Both the anti-incontinence agent 12 and the absorbent article 16 are then enclosed in a pouch 18, see FIG. 1, to keep them in a sanitary and discrete condition. The pouch 18 is formed from a single sheet of material, which has a first end 34 and a second end 36. The first end can be positioned over the second end 36 in an overlapping relationship. Aligned perpendicularly to the first and second ends 34 and 36, respectively, is a first side edge 38 and a second side edge 40, that can be closed and sealed by ultrasonic sealing, heat sealing, adhesive or embossing. The first wrapper 14 and the pouch 18 can be formed from a non-woven material such as a polyolefin, particularly polypropylene or polyethylene. Laminates or co-extruded films including of the mention materials are desirable as well. A desirable thickness is in the range from about 0.005 mm to 0.100 mm.

The anti-incontinence agents 12 can include both medicinal drugs and devices. While devices or surgery are the preferred means for treating stress incontinence, there are many drugs currently developed to treat urge incontinence which mainly focus on the parasympathetic activity of bladder contractions. Drugs with anticholinergic properties are the most common to be used to treat the unstable bladder. A number of other preparations have been used as well. Among these are antispasmodics, tricyclic antidepressants, calcium channel blockers, prostaglandin synthetase inhibitors, and other agents having an effect on smooth muscle contractility, such as potassium channel modulators. Agents typically used include oxybutynin, propantheline, imipramine, terodiline, dicyclomine, and flurbiprofen. These drugs are usually administered orally while some can also be administered as a transdermal patch or as a vaginal or rectal suppository. Drugs that are inhaled or injected are also considered. One such drug is Detrol® available from Pharmacia and Upjohn AB, Sweden. These drugs are associated with a number of side effects, however, which limit their usefulness and create the need for additional incontinence protection in form of an absorbent article or a device and an absorbent article. As a further advantage, drugs could be packaged with absorbent articles to last a pre-determined time period. For instance, in a ratio of two drugs, in the form of pills to last 12 hours each, and three absorbent articles, to last 8 hours each, to meet a daily need in the management of incontinence.

Figure 5:
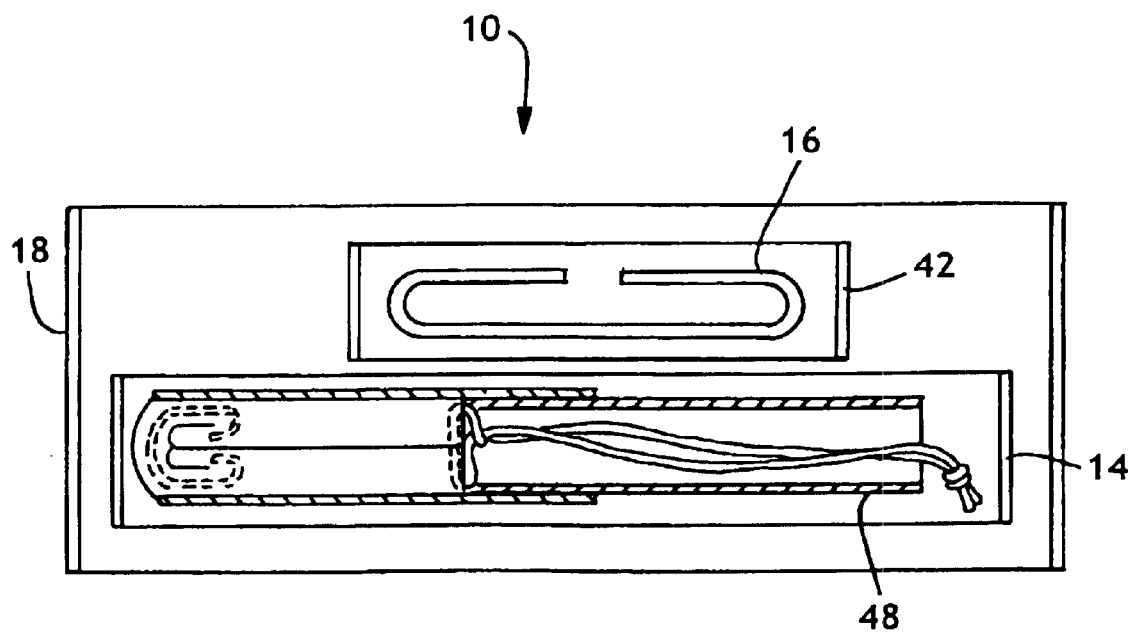
FIG. 5 is a cross-sectional view of a pouch shown in FIG. 1 taken along the line 2—2 showing another alternative combination as a wrapped vaginal incontinence insert and a wrapped absorbent article.

Devices focus on providing support to the bladder through the vaginal wall or preventing leakage of urine through the urethra. Due to pelvic floor weakness, organs prolapse and incontinence may result. Devices that correct this situation by supporting the bladder neck are known as pessaries or vaginal incontinence inserts. Women who leak urine during exercise and other physical activities may benefit from pelvic support from a pessary or vaginal incontinence insert. Urinary control inserts are inserted in the urethra to prevent leakage. The device resides in the urethra and bladder neck. They are available for women who have slight urinary incontinence episodes. The device is inserted using an applicator and is left in until the women needs to void. After removal, the device is discarded. One example of a device is taught is U.S. Pat. No. 6,090,038 which issued to Zunker et al. on Dec. 21, 1998 this patent is entitled, "An Expandable Dome-Shaped Urinary Incontinence Device," also known as a vaginal incontinence insert. This patent is incorporated by reference and made a part hereof. A vaginal incontinence insert 48 is depicted in FIG. 5.

Absorbent articles 16 are designed to absorb body fluids, including urine or menses, and may come in different functional designs. Panty liners or shields are thin products, externally worn about the pudendal area and are designed primarily for very light urine loss. Intra-labial inserts are thin products internally worn inside the labia and are designed for very light urine loss. Sanitary pads or napkins are thin products externally worn about the pudendal area and are designed for light urine loss. Undergarments and protective underwear or refastenable protective underwear are designed for medium to heavy urine loss. Briefs are designed for heavy urine loss. In a final category of absorbent articles, absorbent inserts are used to supplement the absorbency of many of the previously listed absorbent articles. One example of an absorbent article is a POISE® Pad available from Kimberly-Clark Corporation having an office located at 501 North Lake Street, Neenah, Wis. 54956.

Figure 2:
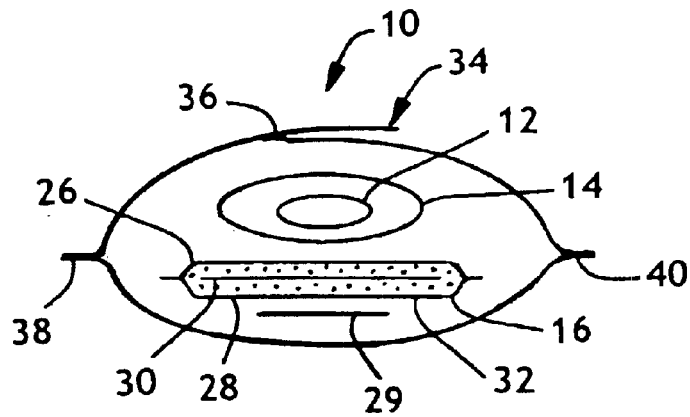
FIG. 2 is a cross-sectional view of the pouch shown in FIG. 1 taken along the line 2—2 showing the combination as a wrapped anti-incontinent agent and an absorbent article.
Figure 3:
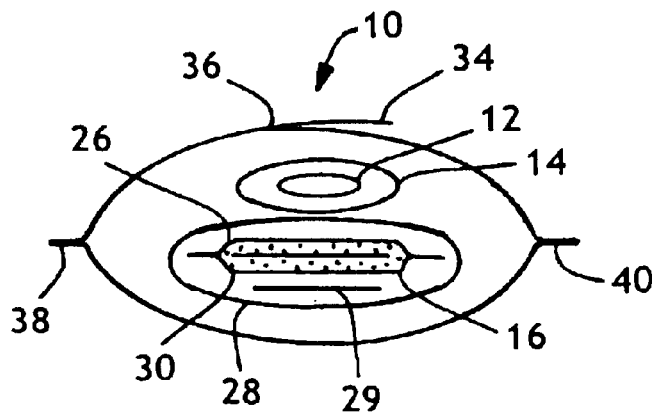
FIG. 3 is a cross-sectional view of the pouch shown in FIG. 1 taken along the line 3—3 showing an alternative combination where the anti-incontinent agent and the absorbent article are wrapped.

Referring to FIGS. 2 and 3, the absorbent article 16 may have a liquid pervious top sheet 26 a liquid impervious back sheet 28 and an absorbent core 30 disposed therebetween. The absorbent article 16 may also contain a peel strip 29. The absorbent core 30 may also contain super absorbent polymer 32. Superabsorbent is a material that is capable of absorbing at least 10 grams of aqueous liquid (e.g. distilled water) per gram of absorbent material while immersed in the liquid for 4 hours and which holds substantially all of the absorbed aqueous liquid while under a compression force of up to about 1.5 psi. Suitable super absorbent polymer is DOW 2035 available from the DOW chemical Company of Midland, Mich. The liquid pervious topsheet 26 is designed to contact the body of the wearer and can be constructed of a woven or non-woven material, which is easily penetrated by body fluid. The liquid pervious topsheet 26 can also be formed from either natural or synthetic fibers. Suitable materials include bonded-carded webs of polyester, polypropylene and polyethylene, linear low-density polyethylene. Finely perforated film webs and net materials also work well. A desirable material is a composite of an apertured thermoplastic film positioned above a non-woven fabric material. Such a composite material can be formed by extrusion of a polymer onto a web of spunbond material to form an integral sheet. One example of this material is an apertured, thermoplastic polyethylene film bonded to a spunbond material. Spunbond is also a desirable topsheet. Spunbond material is a non-woven material, which is manufactured and commercially sold by Kimberly-Clark Corporation having an office located at 501 North Lake Street, Neenah, Wis. 54956.

The liquid impervious back sheet 28 is designed block the passage of body fluid. The liquid impervious backsheet 28 can be made from any material having these properties. A good material from which the liquid impervious backsheet 28 can be constructed is a micro-embossed, polymeric film, such as polyethylene or polypropylene. Bi-component films can also be used. A desirable material is polyethylene film with a thickness in the range from about 0.005 mm to 0.100 mm. Suitably, the liquid impervious backsheet 28 may have a pore size to permit the passage of air out of the article for comfort.

In some embodiments, a peel strip 29 is placed on one side of the absorbent article 16 and is designed to be removed by the user prior to the inner crotch portion of his or her undergarment. The peel strip 29 can be a white Kraft paper which can be coated with a silicone such as a silicone polymer commercially available from Akrosil having an office located at 206 Garfield Avenue, Menasha, Wis. 54952.

The absorbent core 30 can be any absorbent member, which may be compressible, conformable, non-irritating to the wearer's skin, and capable of absorbing and retaining liquid such as urine and other certain body exudates. The absorbent core 30 may be manufactured in a wide variety of sizes and shapes, including but not limited to rectangular, hourglass, "T"-shaped, or asymmetric. The absorbent core 30 may be manufactured from a wide variety of liquid-absorbent materials commonly used in disposable diapers and other absorbent articles. One such material is comminuted wood pulp, which is generally referred to as airfelt. Examples of other suitable absorbent materials include again without limitation, creped cellulose wadding; meltblown polymers including coform, chemically stiffened, modified or cross-linked cellulosic fibers; tissue including tissue wraps and tissue laminates, absorbent foams, absorbent sponges superabsorbent polymers, absorbent gelling materials, or any equivalent material or combination of materials.

Figure 4:
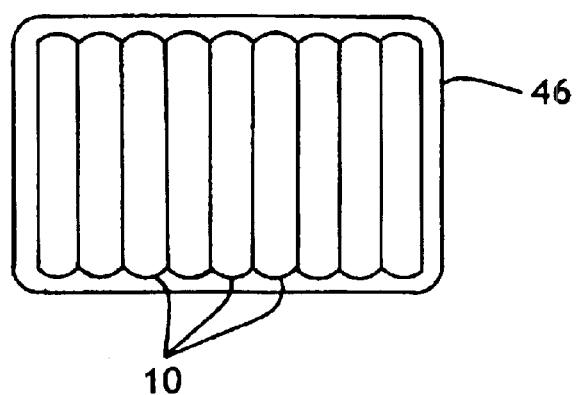
FIG. 4 is a plan view of a package containing a plurality of combinations.

Referring now to FIG. 4 a plurality of combinations 10 can be stacked and placed into a package 46. The package 46 generally has the shape of a rectangle in its cross direction and represents a filled bag containing the containing compressed combinations 10. The package 46 can be made of paper, or any recyclable or biodegradable material and laminate structures comprised of two or more of the aforementioned materials. In addition the package 46 may also be made of non-biodegradable or non-recyclable materials, such as a polymeric film.

Figure 6:
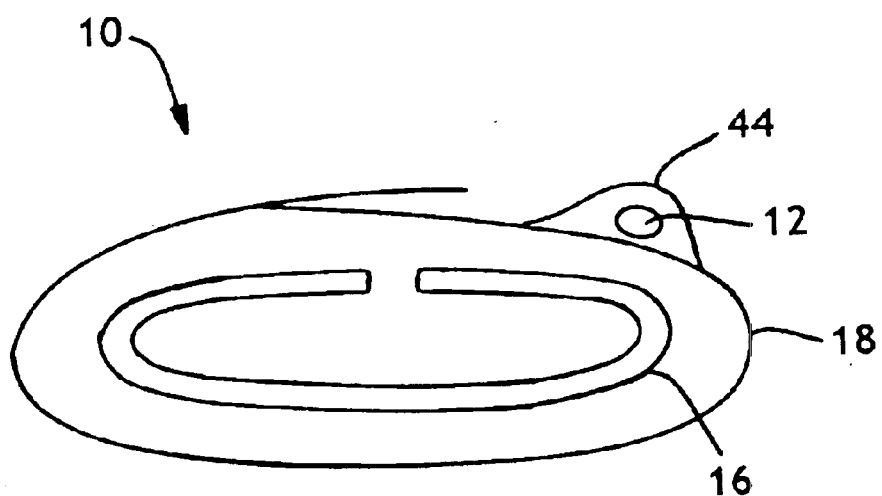
FIG. 6 is a cross-sectional view of still another combination of a drug that is blister packed to the wrapped absorbent article.

Referring now to FIG. 6, the combination 10 includes an anti-incontinence agent 12 in the form of a drug 20, which is enclosed in a blister pack 44. The blister pack 44 can attached to the outside surface of the pouch 18. A film, foil or non-woven material such as a polyolefin, particularly polypropylene or polyethylene or any such material sufficient to maintain a drug's efficacy can form the blister pack 44.

Figure 7:
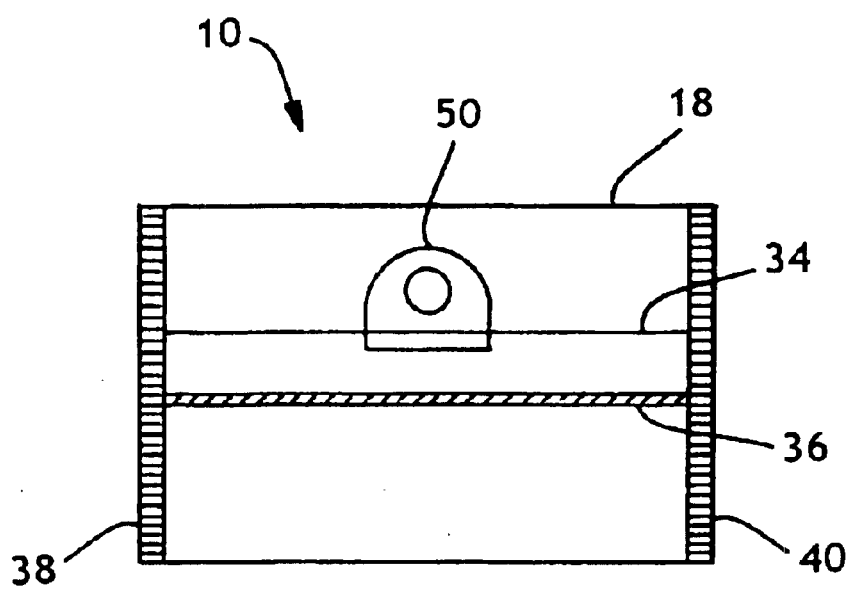
FIG. 7 is a plan view of a pouch showing an opening tab.

Referring now to FIG. 7, the combination liquid pervious top sheet 26 a liquid impervious back sheet 28 of the absorbent article 16 may be enclosed in a pouch 18 that may also contain an opening mechanism. In this case, an opening tab 50 is attached to the second end 36 between the first side edge 38 and the second side edge 40. It is desirable that the opening tab 50 contains a hole in its center to provide an ergonomic means for grasping and pulling the pouch 18 open. The opening tab 50 can be made from a lightweight plastic, such as polyolefin, particularly polypropylene or polyethylene.

Figure 8:
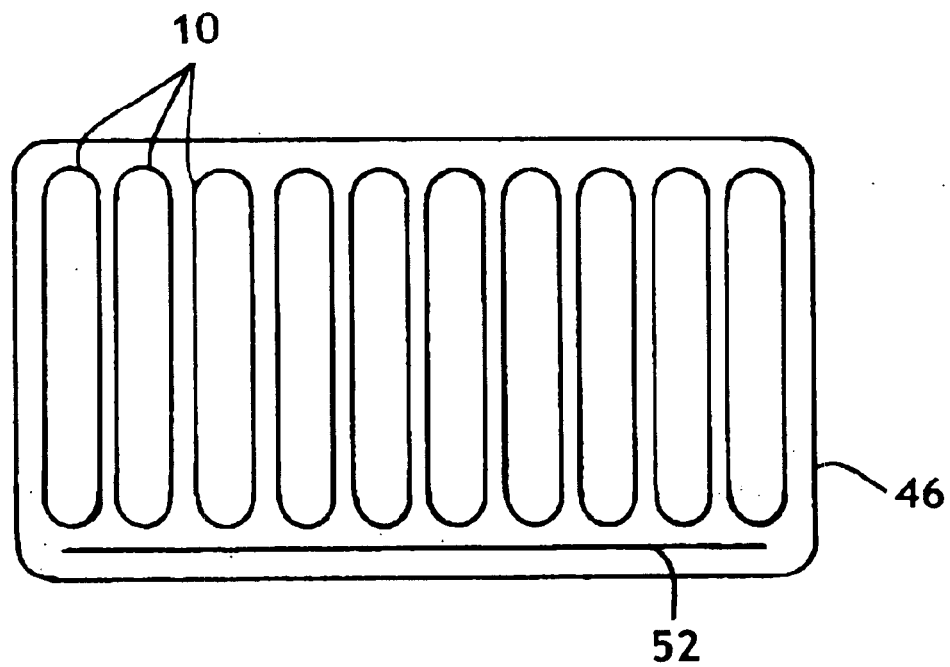
FIG. 8 is a plan view of a package containing a plurality of absorbent articles and written information.
Figure 9:
FIG. 9 depicts an example of written information.

Referring now to FIGS. 8–9, the package 46 can contain written information such as a coupon 52 for a specific drug. For example, the coupon 52 can describe the drug DETROL® as specifically shown in FIG. 9. Written information may also educate the consumer about urinary incontinence and the methods of treating urinary incontinence including but not limited to drugs and devices.

Method of Manufacturing

Figure 10:
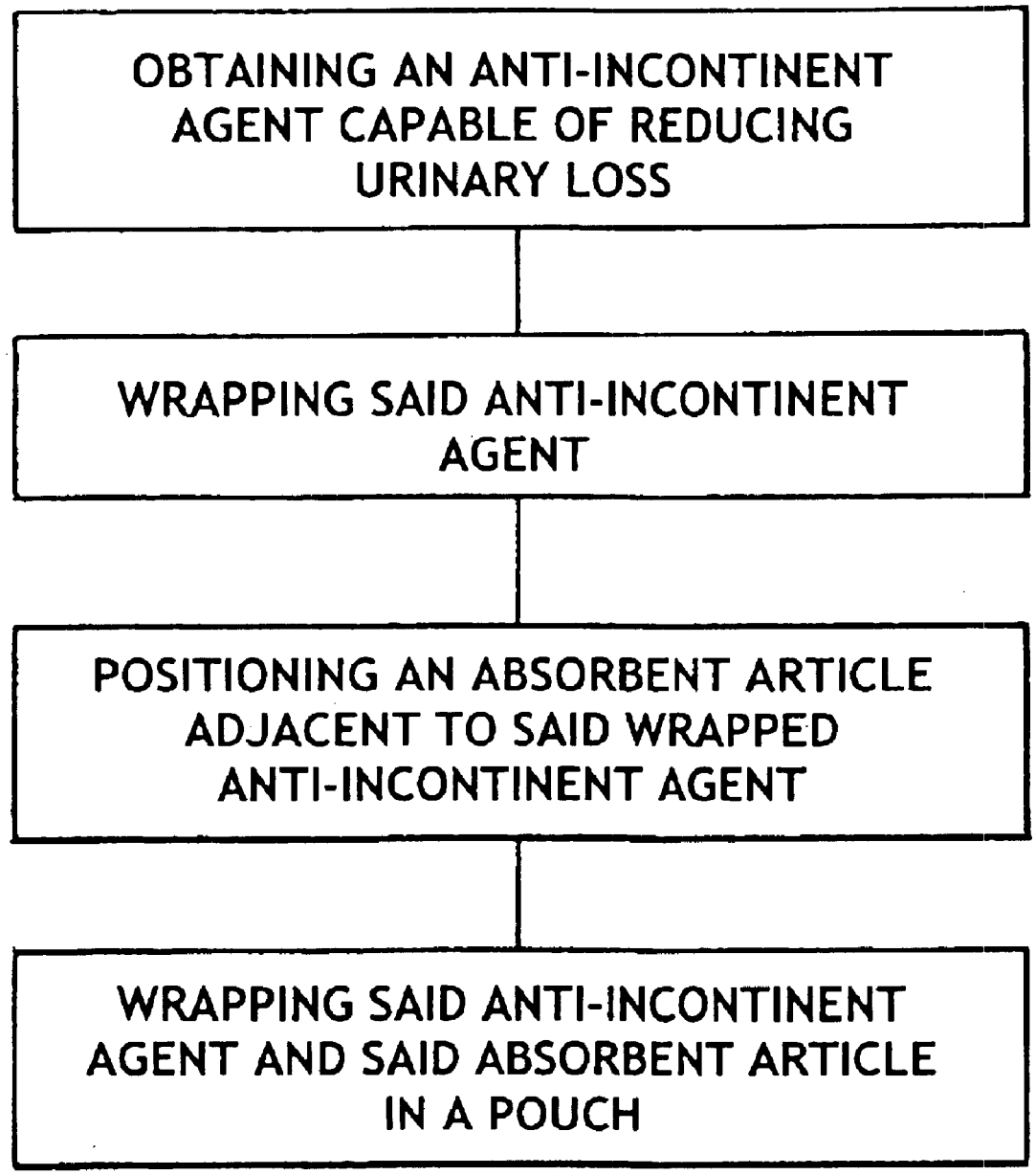
FIG. 10 is a flow diagram of a method of manufacturing a combination for managing the involuntary loss of bladder control.

Referring now to FIG. 10, a method of manufacturing the combination 10 will be explained with reference to the flow diagram. The method includes the steps of obtaining an anti-incontinent agent 12, capable of reducing urinary loss. As described before, this could be a drug 20, or a device 22, or most desirably, a vaginal incontinence insert 48. The anti-incontinence agent 12 is then enclosed in a first wrapper 14. The first wrapper 14 is made of a thin sheet of material, such as a polyethylene, and is then cut to a desired length and placed on a continuously moving belt. The anti-incontinence agent 12, is then placed on one half of the first wrapper 14, and the second half of the first wrapper 14 is folded over the top of the anti-incontinence agent 12, and may be sealed on the first and second ends 34 and 36, and the first and second side edges 38 and 40. Next an absorbent article 16 is positioned adjacent to the wrapped anti-incontinence agent 12. The two items are placed on half of another thin sheet of material, such as polyethylene, and the second half of the material is folded over the items 12 and 16 and sealed on the first and second side edges 38 and 40 to enclose the combination 10 in a pouch 18. The first and second side edges 38 and 40 can be sealed by ultrasonic sealing, heat sealing, adhesive, or embossing.

Method of Using the Combination

Figure 11:
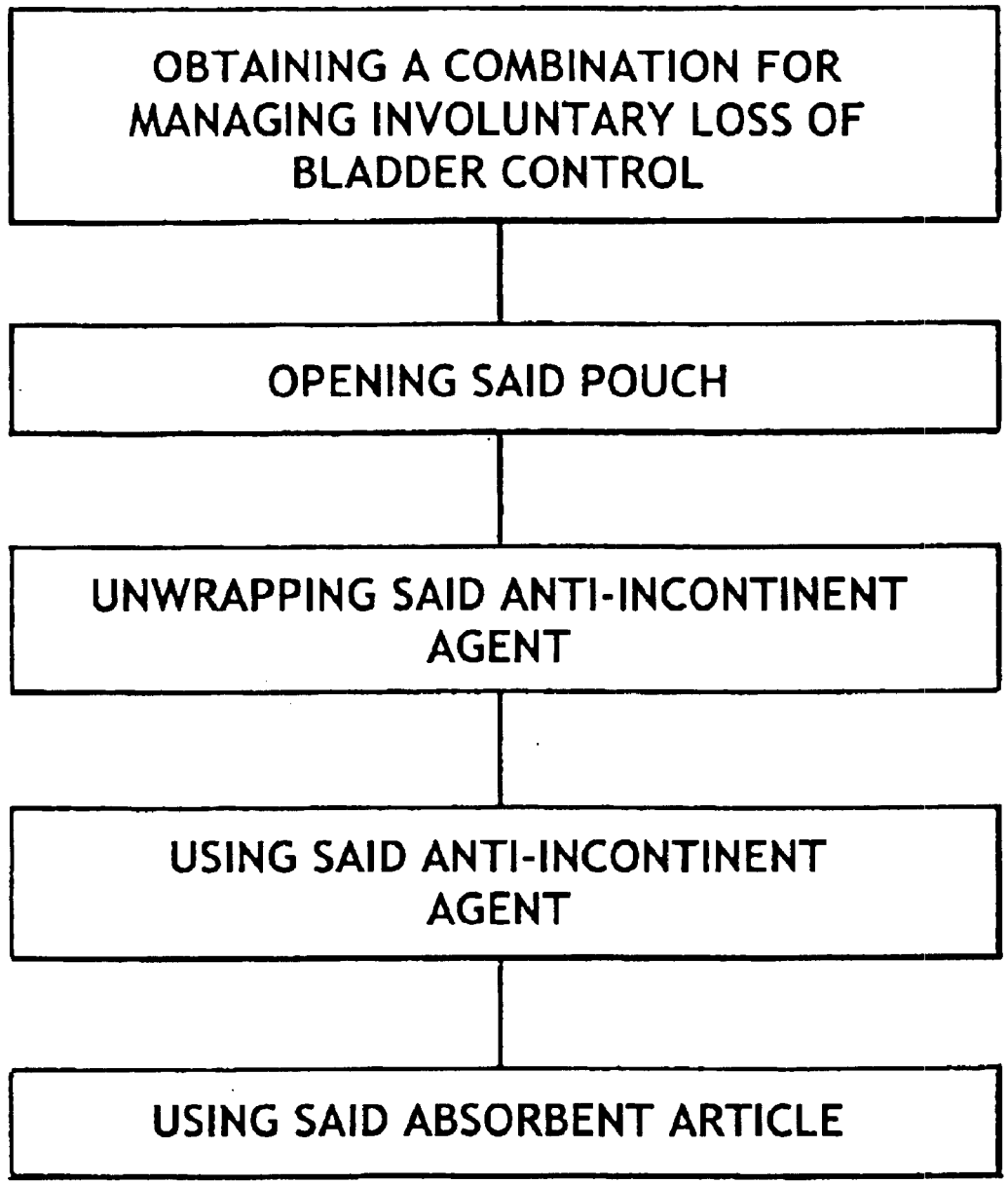
FIG. 11 is a flow diagram of a method for using a combination for managing the involuntary loss of bladder control.

Referring now to FIG. 11, a method for using the combination 10 will be explained with reference to the flow diagram. The method includes the steps of obtaining the combination 10 for managing the involuntary loss of bladder control containing an anti-incontinence agent 12, for example, a drug 20, and an absorbent article 16, for example, a sanitary napkin. The user opens the pouch 18 and then opens the first wrapper 14 around the drug 20 and takes the drug 20 and swallows it. Then the user takes the absorbent article 16, removes the peel strip 29, and places it in his or her underwear. Alternatively, the user could use the absorbent article 16 first and then take the drug 20 last.

While the invention had been described in detail with respect to specific embodiments thereof, it will be appreciated that those skilled in the art upon attaining an understanding of the foregoing may readily conceive of alterations to, variations of and equivalents to these embodiments. Accordingly, the scope of the present invention should be assessed as that of the appended claims and any equivalents thereto.

We claim:

1. A combination for managing the involuntary loss of bladder control comprising:
   a) an anti-incontinent agent capable of reducing urinary loss, said anti-incontinent agent being a drug that can be orally administered;
   b) a first wrapper enclosing said anti-incontinent agent;
   c) an absorbent article positioned adjacent to said wrapped anti-incontinent agent, said absorbent article capable of absorbing urine that is involuntarily lost; and
   d) a pouch enclosing said wrapped anti-incontinent agent and said absorbent article to reduce the likelihood of embarrassing incontinent incidents, said pouch having a first end and a second end, and a first side edge and a second side edge formed between said first and second ends, respectively, and said first end is folded over said absorbent article and overlaps said second end.

2. The combination of claim 1 wherein said drug is capable of inhibiting bladder contractions.

3. The combination of claim 1 wherein said anti-incontinent agent is a device capable of supporting the bladder neck.

4. The combination of claim 1 wherein said anti-incontinent agent is a device capable of obstructing the urethra.

5. The combination of claim 1 wherein said absorbent article is disposable and constructed of a liquid pervious topsheet, a liquid impervious backsheet joined to said topsheet, and an absorbent core disposed between said topsheet and said backsheet, said absorbent core containing super absorbent polymer.

6. The combination of claim 1 wherein said first wrapper and said pouch are formed of different materials.

7. A combination for managing the involuntary loss of bladder control comprising:
   a) an anti-incontinent agent capable of reducing urinary loss, said anti-incontinent agent being a drug that can be transdermally administered;
   b) a first wrapper enclosing said anti-incontinent agent;
   c) an absorbent article positioned adjacent to said wrapped anti-incontinent agent, said absorbent article capable of absorbing urine that is involuntarily lost; and
   d) a couch enclosing said wrapped anti-incontinent agent and said absorbent article to reduce the likelihood of embarrassing incontinent incidents, said pouch having a first end and a second end, and a first side edge and a second side edge formed between said first and second ends, respectively, and said first end is folded over said absorbent article and overlaps said second end.

8. A combination for managing the involuntary loss of bladder control comprising:
   a) an anti-incontinent agent capable of reducing urinary loss;
   b) a first wrapper enclosing said anti-incontinent agent;
   c) an absorbent article positioned adjacent to said wrapped anti-incontinent agent, said absorbent article capable of absorbing urine that is involuntarily lost; and
   d) a pouch enclosing said wrapped anti-incontinent agent and said absorbent article to reduce the likelihood of embarrassing incontinent incidents, said pouch having a first end and a second end and a first side edge and a second side edge formed between said first and second ends, respectively, and said first end is folded over said absorbent article and overlaps said second end.

9. A combination for managing the involuntary loss of bladder control comprising:
   a) an drug capable of reducing urinary loss;
   b) a first wrapper enclosing said drug;
   c) an absorbent article positioned adjacent to said drug, said absorbent article capable of absorbing urine that is involuntarily lost;
   d) a second wrapper enclosing said disposable absorbent article; and
   e) a pouch enclosing said wrapped drug and said wrapped disposable absorbent article to reduce the likelihood of embarrassing incontinent incidents.

10. The combination of claim 9 wherein said drug is administered orally.

11. The combination of claim 10 wherein said first wrapper is a blister pack.

12. The combination of claim 11 further comprising written information inserted into said package.

13. The combination of claim 9 wherein said drug is administered transdermally.

14. The combination of claim 13 wherein there are a plurality of said disposable absorbent articles assembled into a package.

15. A combination for managing the involuntary loss of bladder control comprising:
   a) a vaginal insert capable of supporting the bladder neck;
   b) a first wrapper enclosing said vaginal insert;
   c) a disposable absorbent article positioned adjacent to said wrapped vaginal insert, said disposable absorbent article capable of absorbing urine that is involuntarily lost;
   d) a second wrapper enclosing said disposable absorbent article; and
   e) a pouch enclosing said wrapped vaginal insert and said wrapped disposable absorbent article to reduce the likelihood of embarrassing incontinent incidents.

16. The combination of claim 15 wherein said vaginal insert is expandable and non-absorbent.

17. The combination of claim 16 wherein said pouch has a first end, a second end, a first edge and a second side edge formed between said first and second ends, said first end is folded over said absorbent article and overlaps said second end.

18. The combination of claim 17, further comprising wherein an opening tab which protrudes from said overlapping first end, said opening tab providing a way to open said combination.

19. A method of manufacturing a combination for managing the involuntary loss of bladder control comprising the steps of:
   a) obtaining an anti-incontinent agent capable of reducing urinary loss;
   b) wrapping said anti-incontinent agent;
   c) positioning an absorbent article adjacent to said wrapped anti-incontinent agent, and
   d) wrapping said anti-incontinent agent and said absorbent article in a pouch, said pouch having a first end, a second end, a first side edge, a second side edge formed between said first and second ends, said first end is folded over said absorbent article and overlaps said second end.

20. A method of managing the involuntary loss of bladder control comprising the steps of:
a) obtaining an anti-incontinent agent capable of reducing urinary loss; containing:
   a first wrapper enclosing said anti-incontinent agent;
   an absorbent article positioned adjacent to said wrapped anti-incontinent agent, said absorbent article capable of absorbing urine that is involuntarily lost; and
   a pouch enclosing said wrapped anti-incontinent agent and said absorbent article to reduce the likelihood of embarrassing incontinent incidents;
b) opening said pouch enclosing said wrapped anti-incontinent agent and said absorbent article;
c) unwrapping said wrapped anti-incontinent agent;
d) using said anti-incontinent agent capable of reducing urinary loss; and
e) using said absorbent article capable of absorbing urine that is involuntarily lost to reduce the likelihood of embarrassing incontinent incidents.

21. A combination for managing the involuntary loss of bladder control comprising:
a) a disposable absorbent article constructed of a liquid pervious topsheet, a liquid impervious backsheet joined to said topsheet, and an absorbent core disposed between said topsheet and said backsheet, said absorbent core containing super absorbent polymer and;
b) written information related to an anti-incontinent agent, said written information being a coupon for a drug.

* * * * *